United States Patent [19]

Bundy

[11] 4,130,720

[45] Dec. 19, 1978

[54] 9-DEOXY-9-METHYLENE-PGF-P-SUB-STITUTED PHENYL ESTERS

[75] Inventor: Gordon L. Bundy, Portage, Mich.

[73] Assignee: The Upjohn Company, Kalamazoo, Mich.

[21] Appl. No.: 894,272

[22] Filed: Apr. 7, 1978

Related U.S. Application Data

[63] Continuation-in-part of Ser. No. 786,250, Apr. 11, 1977, Pat. No. 4,098,805.

[51] Int. Cl.$^2$ .......................................... C07C 177/00
[52] U.S. Cl. ...................................... 560/61; 560/55; 560/50; 560/19; 560/106
[58] Field of Search ...................... 560/61, 55, 50, 19, 560/106

[56] References Cited

PUBLICATIONS

Derwent Abstract 05786u–BC NL7209738–Q 16-0-1-73.
Derwent Abstract 76383T–B NL.7206361–Q 14-11-72.
Derwent Abstract 76428W/46 J50071-650 13.06.75.

*Primary Examiner*—Paul J. Killos
*Attorney, Agent, or Firm*—Robert A. Armitage

[57] ABSTRACT

The present invention relates to novel 9-deoxy-9-methylene-p-substituted phenyl esters. These compounds are useful pharmacological agents, and are useful for the same purposes as the corresponding 9-deoxy-9-methylene-PGF-type acids.

17 Claims, No Drawings

9-DEOXY-9-METHYLENE-PGF-p-SUBSTITUTED PHENYL ESTERS

CROSS REFERENCE TO RELATED APPLICATIONS

This application is a continuation-in-part of Ser. No. 786,250, filed Apr. 11, 1977, now U.S. Pat. No 4,098,805, issued July 4, 1978.

The present invention relates to novel 9-deoxy-9-methylene-PGF-p-substituted phenyl esters, the essential material consituting a disclosure of which is incorporated here by reference from U.S. Pat. 4,098,805.

I claim:

1. A prostaglandin analog of the formula

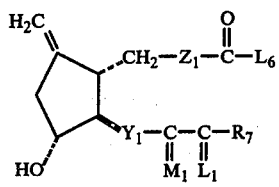

wherein $Y_1$ is trans—CH=CH—, —C≡C—, or —CH$_2$CH$_2$— wherein $M_1$ is

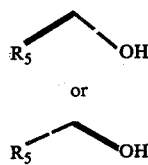

or

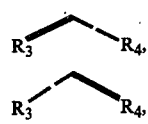

wherein $R_5$ is hydrogen or methyl;
wherein $L_1$ is

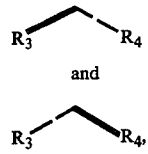

or a mixture of and wherein $R_3$ and $R_4$ are hydrogen, methyl, or fluoro, being the same or different, with the proviso that one of $R_3$ and $R_4$ is fluoro only when the other is hydrogen or fluoro;
wherein $Z_1$ is
(1) cis—CH=CH—CH$_2$—(CH$_2$)$_g$—CH$_2$—,
(2) cis—CH=CH—CH$_2$—(CH$_2$)$_g$—CF$_2$—,
(3) cis—CH$_2$—CH=CH—(CH$_2$)$_g$—CH$_2$—,
(4) —(CH$_2$)$_3$—(CH$_2$)$_g$—CH$_2$—,
(5) —(CH$_2$)$_3$—(CH$_2$)$_g$—CF$_2$—,
(6) —CH$_2$—O—CH$_2$—(CH$_2$)$_g$—CH$_2$—,
(7) —C≡C—CH$_2$—(CH$_2$)$_g$—CH$_2$—,
(8) —CH$_2$—C≡C—(CH$_2$)$_g$—CH$_2$—,

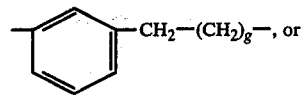

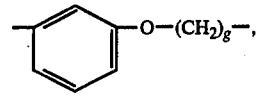

wherein g is one, 2 or 3;
wherein $R_7$ is
(1) —(CH$_2$)$_m$—CH$_3$,

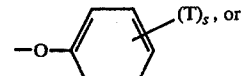

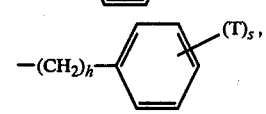

wherein m is one to 5, inclusive, h is zero or one, T is chloro, fluoro, trifluoromethyl, alkyl of one to 3 carbon atoms, inclusive, or alkoxy of one to 3 carbon atoms, inclusive, and s is zero, one, 2, or 3, the various T's being the same or different, with the proviso that not more than two T's are other than alkyl, with the further proviso that $R_7$ is

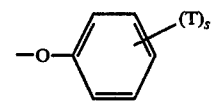

wherein T and s are as defined above, only when $R_3$ and $R_4$ are hydrogen or methyl, being the same or different; and
wherein $L_6$ is p-substituted phenoxy selected from the group consisting of

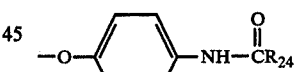

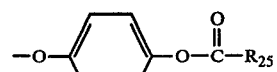

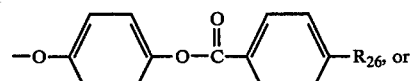

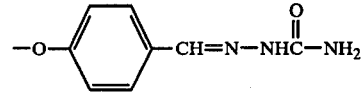

wherein $R_{24}$ is methyl, phenyl, acetamidophenyl, benzamidophenyl, or —NH$_2$; $R_{25}$ is methyl, phenyl, —NH$_2$, or methoxy; and $R_{26}$ is hydrogen or acetamido.

2. A prostaglandin analog according to claim 1, wherein $Y_1$ is —CH$_2$CH$_2$—.

3. 9-Deoxy-9-methylene-16,16-dimethyl-13,14-dihydro-PGF$_2$, p-acetamidophenyl ester, a prostaglandin analog according to claim 2.

4. 9-Deoxy-9-methylene-16,16-dimethyl-13,14-dihydro-PGF$_2$, p-benzaldehyde semicarbazone ester, a prostaglandin analog according to claim 2.

5. A prostaglandin analog according to claim 1, wherein Y$_1$ is trans—CH=CH—.

6. A prostaglandin analog according to claim 5, wherein M$_1$ is

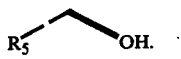

7. 9-Deoxy-9-methylene-16-methyl-15-epi-PGF$_2$, p-benzamidophenyl ester, a prostaglandin analog according to claim 6.

8. A prostaglandin analog according to claim 5, wherein M$_1$ is

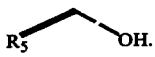

9. A prostaglandin analog according to claim 8, wherein Z$_1$ is aromatic.

10. 3,7-inter-m-Phenylene-3-oxa-4,5,6-trinor-PGF$_2$, p-benzaldehyde semicarbazone ester, a prostaglandin analog according to claim 9.

11. A prostaglandin analog according to claim 8, wherein Z$_1$ is aliphatic.

12. A prostaglandin analog according to claim 11, wherein R$_7$ is

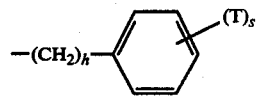

13. 9-Deoxy-9-methylene-16-phenyl-17,18,19,20-tetranor-PGF$_2$, p-acetamidophenyl ester, a prostaglandin analog according to claim 12.

14. A prostaglandin analog according to claim 11, wherein R$_7$ is

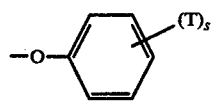

15. 9-Deoxy-9-methylene-15-methyl-16-phenoxy-17,18,19,20-tetranor-PGF$_2$, p-benzaldehyde semicarbazone ester, a prostaglandin analog according to claim 14.

16. A prostaglandin analog according to claim 11, wherein R$_7$ is —(CH$_2$)$_m$—CH$_3$—.

17. 9-Deoxy-9-methylene-16,16-dimethyl-PGF$_2$, p-benzaldehyde semicarbazone ester, a prostaglandin analog according to claim 16.

* * * * *